United States Patent
Hoffman et al.

(10) Patent No.: US 10,516,539 B2
(45) Date of Patent: Dec. 24, 2019

(54) DEVICES, SYSTEMS, AND METHODS FOR AUTHENTICATED INTRAVASCULAR DEVICE USE AND REUSE

(71) Applicant: KONINKLIJKE PHILIPS N.V., Eindhoven (NL)

(72) Inventors: Joseph Hoffman, Sacramento, CA (US); Jason Spencer, Rocklin, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/053,308

(22) Filed: Aug. 2, 2018

(65) Prior Publication Data

US 2018/0343121 A1 Nov. 29, 2018

Related U.S. Application Data

(63) Continuation of application No. 15/914,007, filed on Mar. 7, 2018, now Pat. No. 10,057,066, which is a
(Continued)

(51) Int. Cl.
*H04L 9/32* (2006.01)
*A61B 5/00* (2006.01)
(Continued)

(52) U.S. Cl.
CPC .............. *H04L 9/3242* (2013.01); *A61B 5/00* (2013.01); *A61B 5/0084* (2013.01); *A61B 5/026* (2013.01);
(Continued)

(58) Field of Classification Search
CPC .............................. H04L 9/3242; A61B 90/90
See application file for complete search history.

(56) References Cited

U.S. PATENT DOCUMENTS 9,445,723 B2  9/2016 Hoffman
2004/0167465 A1  8/2004 Mihai
(Continued)

FOREIGN PATENT DOCUMENTS

| JP | 2002197175 A | 7/2002 |
| JP | 2007293618 A | 11/2007 |
| JP | 2010204498 A | 9/2010 |

OTHER PUBLICATIONS

JH Song, J. Lee, T. Iwata, The AES-CMAC, Algorithm (2006), The Internet Society 2006, found at http.//tools.ietf.org/html/rfc4493, pp. 1-20.
(Continued)

*Primary Examiner* — Curtis B Odom

(57) ABSTRACT

Devices, systems, and methods for reconditioning an intravascular device for reuse are provided. The method includes reading first security data from a memory of the intravascular device; determining if the intravascular device is authentic; generating second security data, when the intravascular device is authentic; and writing the second security data to the memory of the intravascular device. Devices, systems, and methods for authenticating an intravascular device for use are also provided. The method includes bringing an intravascular device into communication with a computing device, the intravascular device including a memory; determining if first security data is authentic; determining, when the first security data is authentic, if the intravascular device has been reconditioned; determining, when the intravascular device has been reconditioned, if the second security data is authentic base; and permitting, when second security data is authentic, use of the intravascular device in the clinical procedure.

8 Claims, 3 Drawing Sheets

Related U.S. Application Data continuation of application No. 15/269,692, filed on Sep. 19, 2016, now Pat. No. 9,948,466, which is a continuation of application No. 14/681,892, filed on Apr. 8, 2015, now Pat. No. 9,445,723.

(60) Provisional application No. 61/977,169, filed on Apr. 9, 2014.

(51) Int. Cl.
| | |
|---|---|
| *A61B 5/0215* | (2006.01) |
| *A61B 5/027* | (2006.01) |
| *A61B 90/90* | (2016.01) |
| *A61B 90/94* | (2016.01) |
| *A61B 5/026* | (2006.01) |
| *A61B 8/12* | (2006.01) |
| *A61M 25/00* | (2006.01) |
| *A61B 17/00* | (2006.01) |
| *A61B 90/00* | (2016.01) |
| *A61M 25/09* | (2006.01) |

(52) U.S. Cl.
CPC ............ *A61B 5/027* (2013.01); *A61B 5/0215* (2013.01); *A61B 8/12* (2013.01); *A61B 90/90* (2016.02); *A61B 90/94* (2016.02); *A61B 2017/00482* (2013.01); *A61B 2090/0803* (2016.02); *A61B 2090/0813* (2016.02); *A61B 2090/3735* (2016.02); *A61B 2560/0475* (2013.01); *A61M 25/00* (2013.01); *A61M 25/09* (2013.01); *A61M 2205/52* (2013.01)

(56) References Cited

U.S. PATENT DOCUMENTS

| | | |
|---|---|---|
| 2005/0283210 A1 | 12/2005 | Blischak et al. |
| 2006/0161054 A1 | 7/2006 | Reuss et al. |
| 2007/0282398 A1 | 12/2007 | Healy et al. |
| 2010/0197991 A1 | 8/2010 | Heath |
| 2010/0305442 A1* | 12/2010 | Tierney .................. A61B 8/12 |
| | | 600/443 |
| 2011/0270091 A1 | 11/2011 | Hossack et al. |
| 2013/0061296 A1 | 3/2013 | Reddy et al. |
| 2013/0304061 A1* | 11/2013 | Chang ................ A61B 18/1492 |
| | | 606/41 |

OTHER PUBLICATIONS

Korean Intellectual Property Office, International Search Report for PCT/US2015/024953 dated Jul. 13, 2015, 14 pages.

* cited by examiner

DEVICES, SYSTEMS, AND METHODS FOR AUTHENTICATED INTRAVASCULAR DEVICE USE AND REUSE

CROSS REFERENCE TO RELATED APPLICATIONS

The present application is continuation of U.S. patent application Ser. No. 15/914,007, filed Mar. 7, 2018, which is a continuation of U.S. patent application Ser. No. 15/269,692, filed Sep. 19, 2016, now U.S. Pat. No. 9,948,466, which is a continuation of U.S. patent application Ser. No. 14/681,892, filed Apr. 8, 2015, now U.S. Pat. No. 9,445,723, which claims priority to and the benefit of U.S. Provisional Application No. 61/977,169, filed Apr. 9, 2014, each of which is hereby incorporated by reference in its entirety.

TECHNICAL FIELD

The present disclosure relates generally to intravascular devices with a memory to implement cryptographic algorithms allowing only authorized use and/or reuse of the intravascular devices in clinical procedures.

BACKGROUND

Intravascular devices, such as guide wires, catheters, guide catheters, etc., can be configured for imaging, flow measurement, and/or pressure measurement, among other functions. Such intravascular devices are generally disposable devices. Further, a manufacturer generally rates the intravascular device for a single use. That is, the manufacturer guarantees the safety of the intravascular device and/or the integrity of the data collected using the intravascular device for a single use. After being used within the vasculature of a patient in a clinical procedure, the intravascular device is discarded.

Recently, third parties that are not authorized by the manufacturer have collected used intravascular devices. The used intravascular devices are then sterilized, repackaged, and sold for future use in clinical procedures. This presents significant risk to patients. These intravascular devices have not been verified and validated, and therefore cannot be guaranteed or expected to meet the necessary safety and efficacy standards of an authentic intravascular device. When an intravascular device is inappropriately reused, it can expose patients to direct harm via contamination. It can also expose patients to the possibility of misdiagnosis when a disposable intravascular device is used for a longer time than it was designed to operate safely. In addition to patient safety concerns, a manufacturer also suffers financial losses when customers purchase repackaged, used intravascular devices as opposed to authorized ones.

Some efforts have been made previously to ensure that only authorized intravascular devices are used in clinical procedures. These efforts include preventing the use of intravascular devices whose on-board data did not pass some check conducted by a computing device in the clinical environment. However, third parties have been able to falsify the on-board data so that the computing device treats the intravascular device as authentic.

Further, while a third party without detailed knowledge of the intravascular device is unsuited to reprocess or recondition a used intravascular device, a manufacturer or authorized party is well suited to do so.

Thus, there remains a need for an authentication system that comprehensively prevents the use of unauthorized, fraudulent, and/or otherwise tampered-with intravascular devices. When a manufacturer or an authorized party reconditions a used intravascular device, the authentication system also needs to permit the device to be used in a clinical procedure.

SUMMARY

Embodiments of the present disclosure provide an improved security system for intravascular devices by allowing only authorized use and/or reuse during clinical procedures. The intravascular device includes a memory. Cryptography is implemented using the memory. The improved security also allows a used intravascular device that is properly reconditioned to be reused in a clinical procedure.

In an exemplary aspect, the present disclosure is directed to a method of reconditioning an intravascular device for reuse during a clinical procedure. The method includes reading first security data from a memory of the intravascular device; determining if the intravascular device is authentic based on the first security data; generating second security data, when the intravascular device is authentic; and writing the second security data to the memory of the intravascular device.

In an aspect, the method further includes terminating the reconditioning when the intravascular device is determined to be not authentic. In an aspect, the method further includes sterilizing the intravascular device. In an aspect, the method further includes evaluating performance characteristics of the intravascular device; and generating reuse instructions for the intravascular device based on the performance characteristics. In an aspect, the method further includes reading first device data from the memory of the intravascular device, the first device data including at least one of: a serial number, a manufacturing date, configuration information, initial parameters, a manufacture date, performance parameters, a version number, an expiration date, and system configuration settings. In an aspect, the method further includes generating second device data, the second device including at least one of: a serial number, additional configuration information, additional parameters, a recondition date, reuse instructions, performance parameters, a version number, an expiration date, and system configuration settings; and writing second device data to the memory of the intravascular device. In an aspect, the first and second security data include a message authentication code. In an aspect, the first security data is generated using a secret key, the first device data, and the serial number. In an aspect, the second security data is generated using a secret key, the second device data, and the serial number.

In another exemplary aspect, the present disclosure is directed to an intravascular system. The system includes a computing device in communication with an intravascular device, the computing device being configured to recondition the intravascular device for reuse during a clinical procedure by: reading first security data from a memory of the intravascular device; determining if the intravascular device is authentic based on the first security data; generating second security data, when the intravascular device is authentic; and writing the second security data to the memory of the intravascular device.

In an aspect, the computing device is further configured to: evaluate performance characteristics of the intravascular device; and generate reuse instructions for the intravascular device based on the performance characteristics. In an aspect, the computing device is further configured to: read first device data from the memory of the intravascular device, the first device data including at least one of: a serial number, a manufacturing date, configuration information, initial parameters, a manufacture date, performance parameters, a version number, an expiration date, and system configuration settings; generate second device data, the second device data including at least one of: a serial number, additional configuration information, additional parameters, a recondition date, reuse instructions, performance parameters, a version number, an expiration date, and system configuration settings; and write second device data to the memory of the intravascular device. In an aspect, the computing device is further configured to generate the second security data by generating a message authentication code. In an aspect, the computing device is further configured to generate the second security data by using a secret key, the second device data, and the serial number.

In another exemplary aspect, the present disclosure is directed to a method of authenticating an intravascular device for use during a clinical procedure. The method includes bringing an intravascular device into communication with a computing device, the intravascular device including a memory accessible by the computing device, the memory having first device data, second device data, first security data, and second security data stored thereon; determining if first security data is authentic based on the first device data; determining, when the first security data is authentic, if the intravascular device has been reconditioned based on the second device data; determining, when the intravascular device has been reconditioned, if the second security data is authentic based on the second device data; and permitting, when second security data is authentic, use of the intravascular device in the clinical procedure.

In an aspect, the method further includes determining if the intravascular device is within an authorized period of use based on at least one of the first device data and the second device data; and permitting, when the intravascular device is within the authorized period of use, use of the intravascular device in the clinical procedure. In an aspect, the first and second security data include a message authentication code, wherein the first security data is generated using a secret key, the first device data, and a serial number of the memory, and the second security data is generated using the secret key, the second device data, and the serial number of the memory.

In another exemplary aspect, the present disclosure is directed to an intravascular system. The system includes a computing device in communication with an intravascular device having a memory, the computing device being configured to authenticate the intravascular device for use during a clinical procedure by: determining if first security data stored on the memory is authentic based on first device data stored on the memory; determining, when the first security data is authentic, if the intravascular device has been reconditioned based on second device data stored on the memory; determining, when the intravascular device has been reconditioned, if second security data stored on the memory is authentic based on the second device data; and permitting, when second security data is authentic, use of the intravascular device in the clinical procedure.

In an aspect, the computing device is further configured to: determine if the intravascular device is within an authorized period of use based on at least one of the first device data and the second device data; and permit, when the intravascular device is within the authorized period of use, use of the intravascular device in the clinical procedure. In an aspect, the first and second security data include a message authentication code, wherein the first security data is generated using a secret key, the first device data, and a serial number of the memory, and the second security data is generated using the secret key, the second device data, and the serial number of the memory.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
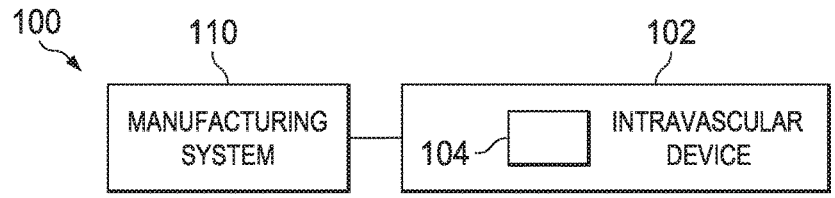
FIG. 1 is a diagrammatic schematic view of an intravascular system in a manufacturing environment according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

The devices, systems, and methods described herein relate to authenticated use and/or reuse of an intravascular device. The intravascular device includes a memory. The authentication scheme described herein implements encryption using the memory. Authentication can be accomplished using one or more cryptographic codes written to the memory of the intravascular device. The authentication scheme described herein uses data about the intravascular device stored on the memory as well as the cryptographic codes to comprehensively prevent unauthorized device use and/or reuse. New data (e.g., about the intravascular device and/or cryptographic codes) can be written to the memory to further secure the intravascular device. For example, new data can be written to the memory before, during, and/or after use, reuse, sterilization, and/or reconditioning of the intravascular device. A computing device in the clinical environment and/or a remote computing device can use the data about the intravascular device and/or the cryptographic codes to verify that the intravascular device is authentic and authorized to be used during the clinical procedure.

The authentication algorithm described herein prevents the use of an expired and/or unauthorized intravascular device by verifying the integrity and status of the intravascular device before use. An intravascular device can be unauthorized when the device is being improperly reused or because the device is an unauthorized clone of the manufacturer's device. The cryptography implemented as part of the memory of the intravascular device makes it computationally infeasible to forge a valid intravascular device such that it would be incorrectly treated as authentic.

The devices, systems, and methods described herein can apply to any disposable or limited use intravascular device, include devices configured for intravascular ultrasound (IVUS), optical coherence tomography (OCT), forward-looking IVUS (FLIVUS), forward-looking intra-cardiac echo (FLICE), flow measurements, pressure measurements, and/or combinations thereof.

FIG. 1 is a diagrammatic schematic view of an intravascular system 100 in a manufacturing environment, according to aspects of the present disclosure. The intravascular system 100 includes an intravascular device 102, such as a catheter, guide wire, or guide catheter. In some embodiments, the intravascular device 102 is configured to image a lumen of a blood vessel using one or more imaging modalities (e.g., IVUS, OCT, etc.). In some embodiments, the intravascular device 102 is configured to measure the pressure and/or flow of blood through the blood vessel. One or more components for imaging, pressure measurement, and/or flow measurement can be positioned at a distal portion of the intravascular device 102.

The intravascular device 102 includes a memory 104. The memory 104 can be a write-once memory or a rewritable/reprogrammable memory. For example, with a rewritable/programmable memory, portions of the memory 104 can be rewritten or reprogrammed, after being initially programmed, without degradation of the memory and/or the intravascular device 102. In various embodiments, the memory 104 can be Electrically Erasable Programmable Read-Only Memory (EEPROM), flash memory, hard disk, and/or other suitable storage. The memory 104 has sufficient capacity to store data about the intravascular device 102 (e.g., unique serial number of the memory 104, configuration information, initial parameters, reuse instructions, manufacturing data, reprocessing data, clinical use data, etc.) as well as security or cryptographic data (e.g., one or more message authentication code(s)).

The intravascular device 102 is a disposable or limited use device. For example, a manufacturer can guarantee the safety of the intravascular device 102 and/or the integrity of the data collected using the intravascular device 102 for one, two, three, four, or more limited number of uses. The intravascular device 102 can also be a reusable device that is sterilizable (e.g., using autoclave procedures) between uses. Thus, the intravascular device 102 can be used in multiple procedures. In some embodiments, the intravascular device 102 is reusable after only being sterilized. In some embodiments, the intravascular device 102 is reusable after being reconditioned (e.g., after being both sterilized and undergoing further processing to prepare the intravascular device 102 for reuse). An exemplary embodiment of a reconditioning procedure is discussed with respect to FIGS. 3 and 4. The intravascular device 102 can be configured for use and/or reuse within a specified period of time after manufacture and/or reconditioning.

FIG. 1 illustrates a manufacturing environment in which the intravascular device 102 is initially assembled, conditioned, and/or programmed. Data about the intravascular device can be written to the memory 104 by the manufacturing system 110. The manufacturing system 110 includes a computing device configured to be in communication with the intravascular device 102 and to program the intravascular device 102 with the initial parameters, the security data, and other suitable data to allow the intravascular device 102 to be used in a clinical environment. An exemplary embodiment of an initial conditioning procedure is discussed with respect to FIG. 2.

The manufacturing system 110 can be configured to directly access, read, and/or write the memory 104. In a manufacturing environment, the communication of signals between the manufacturing system 110 and the intravascular device 102 can include transferring the initial parameters, the security data, and other suitable data from the manufacturing system 110 to the intravascular device 102. In some embodiments, the manufacturing system 110 does not directly access the memory 104, and rather, an additional component (e.g., similar to the patient interface module (PIM) 520 of FIG. 5) facilitates communication between the manufacturing system 110 and the intravascular device 102. In some embodiments, the functionality of the additional component is performed by the manufacturing system 110 and/or the intravascular device 102 such that the additional component is not utilized.

Figure 2:
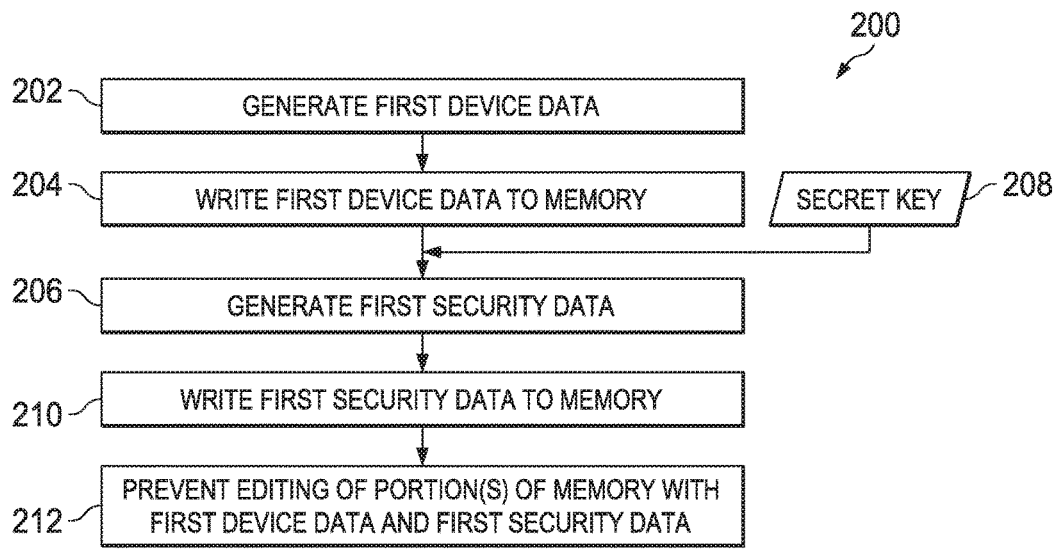
FIG. 2 is a flow diagram of a method of initially conditioning an intravascular device for use during a clinical procedure according to aspects of the present disclosure.

FIG. 2 is a flow diagram of method 200 of initially conditioning an intravascular device for use during a clinical procedure, according to aspects of the present disclosure. One or more steps of the method 200 can be carried out by the manufacturing system 110 to prepare the intravascular device 102 for use in a patient's vasculature. As a result of the method 200, the intravascular device 102 can be implemented along with an authentication algorithm to allow only authorized use and/or reuse of the intravascular device 102.

At step 202, the method 200 includes generating first device data. First device data can include, e.g., a unique serial number of the memory 104, configuration information, initial parameters, a manufacture date, performance parameters, a version number, an expiration date, system configuration settings, and other data about the intravascular device 102. The first device data can be generated based on the particular components of the intravascular device 102, including the memory 104 and the component(s) for imaging, pressure measurement, and/or flow measurement. In some embodiments, the factory-/manufacturing-provided unique serial number can be written on a read-only memory (ROM) portion of the memory 104.

At step 204, the method 200 includes writing the first device data to the memory 104. For example, the intravascular device 102 can be brought into communication with the manufacturing system 110 such that the manufacturing system 110 can access and program the memory 104. The first device data can be written to specified portions of the memory 104 (e.g., pages 0 and 1).

At step 206, the method 200 includes generating first security data. In some embodiments, the first security data (as well as a second, third, fourth, and other security data) can include a message authentication code (MAC) or other suitable cryptographic tool such as hash functions, block ciphers, etc. In some embodiments, the first security data is generated using the first device data, the unique serial number of the memory 104, and a secret key 208 as input.

The secret key 208 can be a parameter used in the authentication algorithm that is known only to the manufacturer of the intravascular device 102 or an authorized party.

In an exemplary embodiment, the authentication algorithm utilizes a cipher-based message authentication code (CMAC) or one-key CBC MAC1 (OMAC1) with the 128-bit advanced encryption standard (AES). An exemplary authentication algorithm is described in *The Internet Society, The AES-CMAC Algorithm* (2006), available at http://tools.ietf.org/html/rfc4493, the entirety of which is hereby incorporated reference. In various embodiments, other suitable authentication schemes, such as the data authentication algorithm (DAC), cipher block chaining message authentication code (CBC-MAC), keyed-hash message authentication code (HMAC), parallelizable MAC (PMAC), VMAC, message authentication code based on universal hashing (UMAC), Poly1305-AES, etc., may be utilized.

One or more MACs for the devices, systems, and methods described herein can be generated as follows for a CMAC-based authentication algorithm. Let k denote a 128-bit key chosen uniformly at random by the manufacturer as the secret key, and let $k_1$, $k_2$ be 128-bit subkeys derived from k as output of the GenerateSubKey algorithm below. Let $E_k(x)$ and $E_k^{-1}(x)$ be the 128-bit AES encryption and decryption functions respectively on a 128-bit string x using key k. Let $msb_1(x)$ denote the most significant (or left-most) bits of x or the most significant bit if 1 is omitted. Left shift is denoted by $<<$ and exclusive-or by $\oplus$.

The GenerateSubKey algorithm can be defined as set forth below. The GenerateSubKey algorithm can take a 128-bit (16-byte) string and return two 128-bit strings to be used as subkeys in the GenerateMac algorithm.

```
GenerateSubKey (k:uint128):(uint128, uint128)
    C ← (uint128)0x87
    k₀ ← Eₖ((unit128)0)
    if msb(k₀) = 0
        k₁ ← k₀ << 1
    else
        k₁ ← (k₀ << 1) ⊕ C
    if msb(k₁) = 0
        k₂ ← k₁ << 1
    else
        k₂ ← (k₁ << 1) ⊕ C
    return (k₁,k₂)
```

The GenerateMac algorithm can be defined as set forth below. The GenerateMac algorithm utilizes the 128-bit key k, a byte array D containing a message to generate a CMAC, and the length n in bytes of D. The return value is the 128-bit CMAC.

```
GenerateMac (k:uint128, D:byte[n], n:int):uint128
    (k₁, k₂) ← GerateSubKey(k)
    if n = 0
        return ERROR
    m ← ⌈n/16⌉         {m is the number of blocks to process}
    B:unit128[m]       {B is the message as 16-byte blocks}
    for i in [0,m - 1]
        B[i] ← D[i * 16]
    if n ≡ 0 (mod 16)
        B [m - 1] ← B[m - 1]⊕k₁
    else {pad the last block with bits 100...00}
        lastBlock:uint128
        lastBlock ← D[((m - 1) * 16) ... n] 0x80 0¹⁶⁻⁽ⁿ⁻¹⁶⁽ᵐ⁻¹⁾⁾⁻¹
        B[m - 1] ← lastBlock⊕k₂
    x ← (unit128)0
    for i in [0,m - 1]
        y ← x ⊕ B[i]
        x ← Eₖ(y)
    return x
```

At step 210, the method 200 includes writing the first security data to the memory 104. The first security data can be written to a specified portion of the memory 104 (e.g., page 1).

At step 212, the method 200 includes preventing editing of the portion(s) of the memory 104 with the first device data and the first security data. For example, the memory 104 can include a lock page functionality that locks specified portions of the memory 104 and prevents those portions from being edited.

Figure 5:
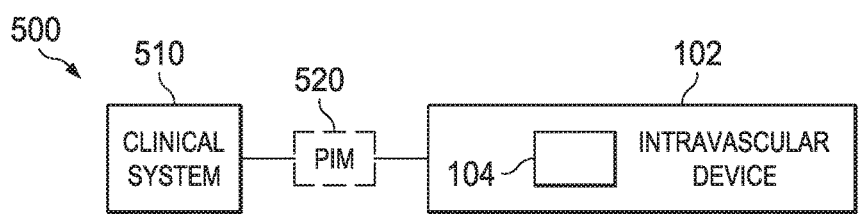
FIG. 5 is a diagrammatic schematic view of an intravascular system in a clinical environment according to aspects of the present disclosure.
Figure 6:
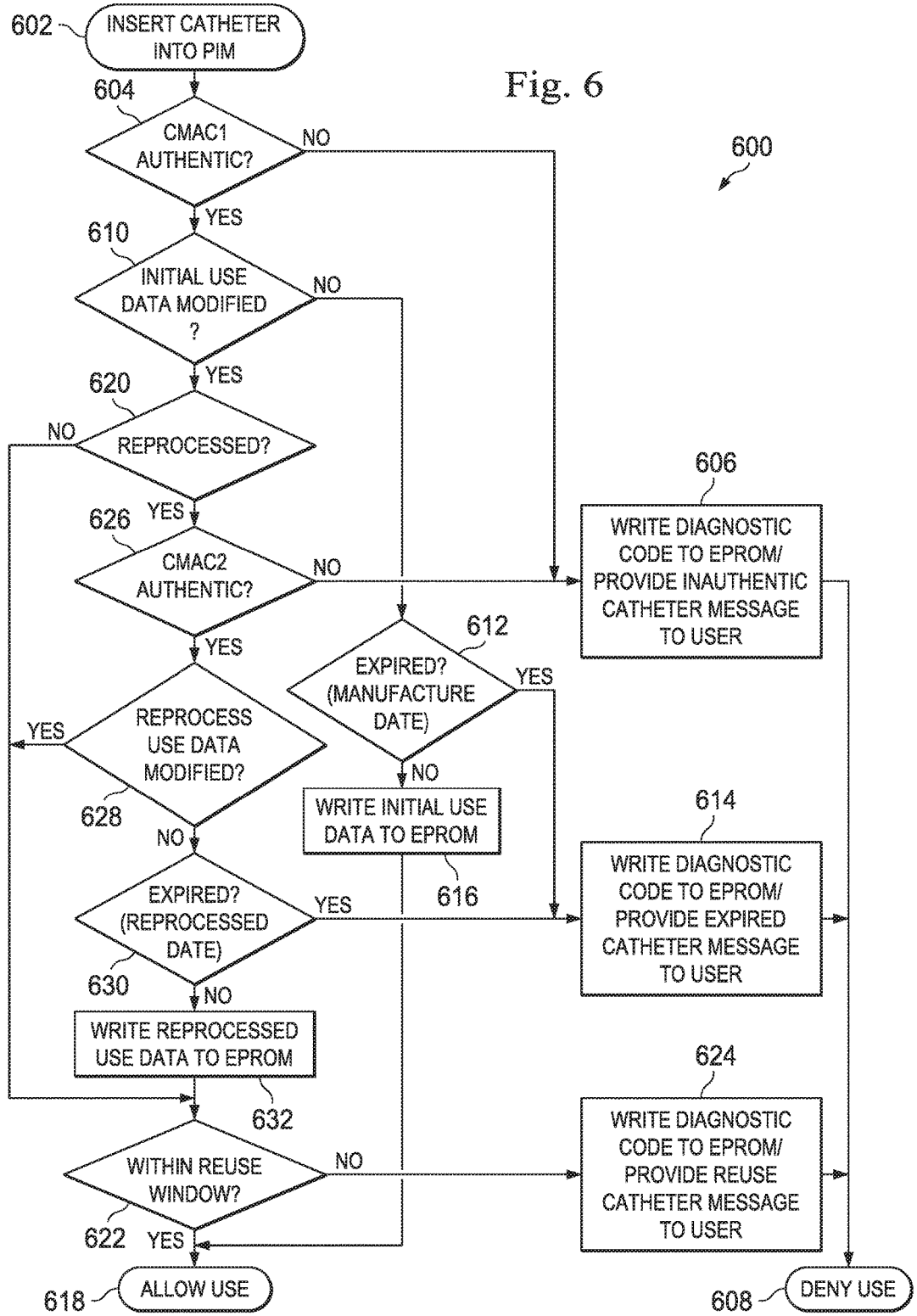
FIG. 6 is a flow diagram of a method of authenticating an intravascular device for use and/or reuse during a clinical procedure according to aspects of the present disclosure.

After being initially conditioned based on the method 200, the intravascular device and the authentication algorithm can be implemented in a clinical environment as described with respect to FIGS. 5 and 6. After one or more uses, the intravascular device can be reconditioned by the manufacturer or authorized party for subsequent uses. This is described with respect to FIGS. 3 and 4.

Figure 3:
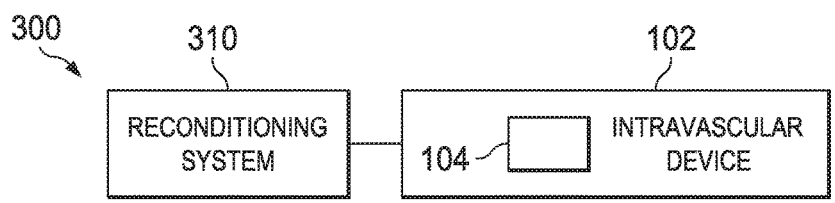
FIG. 3 is a diagrammatic schematic view of an intravascular system in a reconditioning environment according to aspects of the present disclosure.

FIG. 3 is a diagrammatic schematic view of an intravascular system 300 in a reconditioning environment, according to aspects of the present disclosure. FIG. 3 illustrates a reconditioning environment in which the intravascular device 102 is prepared for reuse, after the intravascular device 102 has been used in one or more clinical procedures. A computing device (e.g., a reconditioning system 310) can evaluate performance characteristics of the intravascular device 102 to identify any changes resulting from earlier uses and generate reuse instructions that compensate for the identified changes. The reconditioning system 310 can also write second security data, a recondition date, etc., to the memory 104 such that a clinical system will recognize that the intravascular device 102 has been properly reconditioned and permit reuse. In some embodiments, the reconditioning system 310 can be configured to directly access, read, and/or write the memory 104. In some embodiments, the manufacturing system 110 does not directly access the memory 104, and rather, an additional component facilitates communication between the manufacturing system 110 and the intravascular device 102. In some embodiments, the reconditioning system 310 can be the manufacturing system 110 (FIG. 1). For example, the manufacturing system 110 can be configured to perform the initial conditioning procedure described with respect to FIG. 2 and the reconditioning procedure described with respect to FIG. 4.

Figure 4:
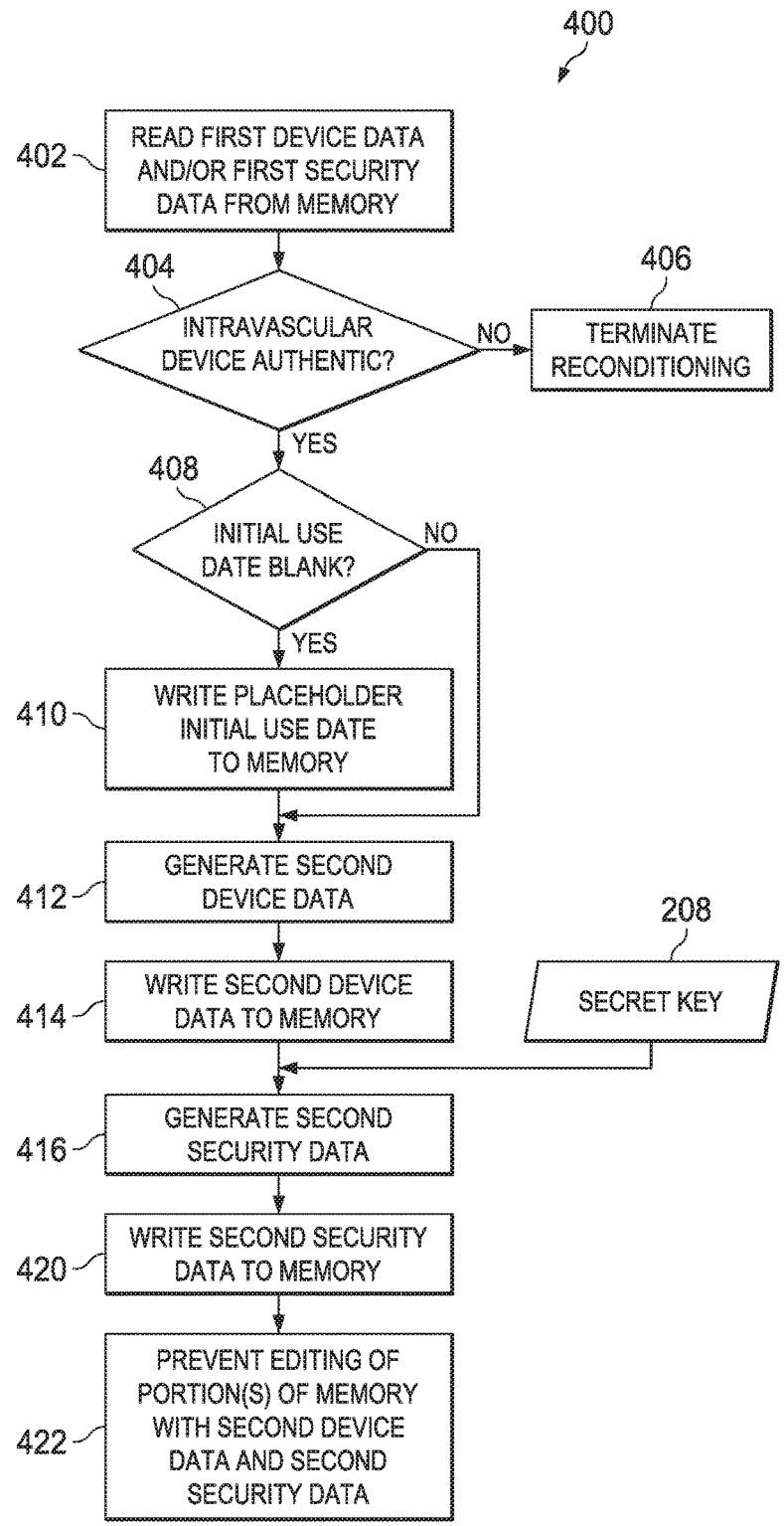
FIG. 4 is a flow diagram of a method of reconditioning an intravascular device for reuse during a clinical procedure according to aspects of the present disclosure.

FIG. 4 is a flow diagram of a method 400 of reconditioning an intravascular device for reuse during a clinical procedure according to aspects of the present disclosure. One or more steps of the method 400 can be carried out by the manufacturer or an authorized party using the reconditioning system 310. As a result of the method 400, the intravascular device 102 can be implemented along with an authentication algorithm to allow only authorized reuse of the reconditioned intravascular device 102 in a clinical environment.

At step 402, the method 400 includes reading the first device data and/or the first security data from the memory 104. At step 404, the method 400 includes determining if the intravascular device 102 is authentic. For example, the reconditioning system 310 can determine that the intravascular device 102 is authentic using the authentication algorithm described herein. Using the first device data read from the memory 104 (step 402), the reconditioning system 310 can determine that the first security data read from the memory 104 (step 402) is authentic. If the intravascular device 102 is not authentic, at step 406, the method 400 can include terminating the reconditioning procedure. Such circumstances can arise, for example, when the intravascular device 102 was not initially conditioned by the manufacturer, the memory 104 was tampered with, etc. In such circumstances, use of the intravascular device 102 may present a health risk to the patient, and the intravascular device 102 can be discarded. In some embodiments, additional processing can be performed if the intravascular device is not authentic to remove the health risks to the patient, re-authenticate the intravascular device, etc. In such embodiments, an intravascular device that is determined to be inauthentic is not discarded and undergoes the reconditioning procedure.

When the intravascular device 102 is authentic, at step 408, the method 400 includes determining if an initial use date field of the memory 104 is blank. Such circumstances can arise, for example, when an intravascular device 102 that has not been previously used is introduced to the reconditioning environment. The initial use field of the memory 104 can also be blank when an intravascular device 102 is previously used but the initial use field was not populated by a computing device in the clinical environment through some error. Even though non-standard events can cause the initial use date field to be blank, those events are not likely to require termination of the reconditioning procedure because the authenticity of the intravascular device (step 404) has already been verified. When the initial use date field is blank, at step 410, a placeholder initial use date can be written to a specified portion of the memory 104 (e.g., page 3).

When the initial use date field has been populated with a placeholder or when the initial use date field is not blank, at step 412, the method 400 can include generating second device data. In some embodiments, the second device data can include all or some portion of the of the first device data. The second device data can include a serial number, additional configuration information, additional parameters, a recondition date, reuse instructions, performance parameters, a version number, an expiration date, system configuration settings, and other data about the intravascular device 102.

In some embodiments, the method 400 can include evaluating performance characteristics of the intravascular device (e.g., one or more component(s) of the intravascular device 102 for imaging, pressure measurement, and/or flow measurement). The performance of the intravascular device 102 can degrade as a natural result of use. The method 400 can thus include generating reuse instructions generated based on the performance characteristics. The reuse instructions can, for example, specify how data collected by the intravascular device 102 should be processed in the clinical environment. The reuse instructions can be a modification of how the data was processed during an initial use and can compensate for any degradation of the intravascular device 102. At step 414, the method 400 includes writing the second device data to the memory 104. The second device data can be written to specified portion(s) of the memory 104 (e.g., page 2).

At step 416, the method 400 includes generating second security data. In some embodiments, the second security data can include a second MAC. The second MAC can be generated in a similar manner as the first MAC described above. For example, the second MAC can be generated using the second device data, all or some portion of the first device data, the unique serial number of the memory 104, and the secret key 208 as input. At step 420, the method 400 includes writing the second security data to the memory 104. The second security data can be written to a specified portion of the memory 104 (e.g., page 2). In some embodiments, the second security data replaces the first security data. For example, the specified portion of the memory 104 including the first MAC is rewritten to include the second MAC. In some embodiments, the memory 104 includes both the first security data and the second security data. At step 422, the method 400 includes preventing editing of the portion(s) of the memory 104 with the second device data and the second security data using the lock page functionality of the memory 104.

After being reconditioned based on the method 400, the intravascular device and the authentication algorithm can be implemented in a clinical environment as described with respect to FIGS. 5 and 6.

FIG. 5 is a diagrammatic schematic view of an intravascular system 500 in a clinical environment, according to aspects of the present disclosure. FIG. 5 illustrates a clinical environment in which the intravascular device 102 is used and/or reused during a clinical procedure. For example, the intravascular device 102 can be used with a clinical system 510 for intravascular imaging, pressure measurement, and/or flow measurement. The clinical system 510 can include a computing device in communication with the intravascular device 102 and configured to determine if the intravascular device 102 is authenticated for use and/or reuse.

The clinical system 510 and the intravascular device 102 can be in communication a patient interface module (PIM) 520 in some embodiments. The PIM 520 facilitates communication of signals between the clinical system 510 and the intravascular device 102. In some embodiments, the PIM 520 supplies high- and low-voltage DC power to support operation of the intravascular device 102, including the component(s) for imaging, pressure measurement, and/or flow measurement. In some embodiments, the PIM 520 is configured to access, read, and/or write the memory 104 based on, e.g., instructions from the clinical system 510. In other embodiments, the clinical system 510 is configured to directly access, read, and/or write the memory 104 without the PIM 520.

FIG. 6 is a flow diagram of a method 600 of authenticating an intravascular device for use and/or reuse during a clinical procedure according to aspects of the present disclosure. One or more steps of the method 600 can be carried out by using the clinical system 510. The method 600 can allow for authenticated initial use of the intravascular device 102, authenticated reuse of the intravascular device 102, authenticated initial use of a reconditioned intravascular device 102, and/or authenticated reuse of the reconditioned intravascular device 102.

At step 602, the method 600 includes bringing the intravascular device 102 into communication with the PIM 520 and/or the clinical system 510. For example, a catheter can be physically inserted into the PIM 520. In other embodiments, the intravascular device 102 wirelessly communicates with the PIM 520 and/or the clinical system 510.

At step 604, the method 600 includes determining if the first security data is authentic. For example, the clinical system 510 can determine if the first MAC is authentic using the first device data. If the first security data is not authentic, the intravascular device 102 is determined to be unauthorized for use. The first security data can be inauthentic when, for example, the data of the memory 104 is forged and/or otherwise tampered with. When the first security data is not authentic, at step 606, the method 600 includes providing an indication to a user that the intravascular device 102 is unauthorized for clinical use. The clinical system 510 can also write a diagnostic code to the memory 104 indicating that the intravascular device 102 is unauthorized because the security data is not authentic. For example, the clinical system 510 will modify a first unused use date field of the memory 104, write the serial number of the clinical system 510 to the memory 104, and/or write the diagnostic code to the memory 104. Future attempted reuse of the unauthorized intravascular device 102 can be prevented when a clinical system reads the diagnostic code. At step 608, the method 600 includes denying use of the intravascular device 102.

When the first security data is authentic, at step 610, the method 600 includes determining if the initial use date field of the memory 104 has been modified. When the initial use date field has not been modified, the clinical system 510 determines that the intravascular device 102 is a new, unused device. To determine if the intravascular device 102 is authorized for initial use, at step 612, method 600 includes determining if the intravascular device 102 has expired. Step 612 can include reading the manufacture date field and/or an authorized period of use field from the memory 104. The clinical system 510 can determine if a current date, compared to the manufacture date, is within authorized period of use. If the intravascular device 102 is determined to be expired, then the intravascular device 102 is not authorized. At step 614, the method 600 includes providing an indication to a user that the intravascular device 102 is unauthorized for clinical use. The clinical system 510 can also write a diagnostic code to the memory 104 indicating that the intravascular device 102 is unauthorized because the intravascular device 102 has expired. For example, the clinical system 510 will modify a first unused use date field of the memory 104, write the serial number of the clinical system 510 to the memory 104, and/or write the diagnostic code. Future attempted reuse of the unauthorized intravascular device 102 can be prevented when a clinical system reads the diagnostic code. At step 608, the method 600 includes denying use of the intravascular device 102.

When the intravascular device 102 has not expired, the clinical system 510 determines that the intravascular device 102 is authorized for initial use. At step 616, the method 600 includes writing the current date to the initial use date field of the memory 104. Step 616 can also include writing the serial number of the clinical system 510 to the memory 104 as further information regarding use of the intravascular device 102. At step 618, the method 600 includes allowing use of the intravascular device 102.

If the clinical system 510 determines, at step 610, that the initial use date field of the memory 104 has been modified, then, at step 620, the method 600 includes determining if the intravascular device 102 has been reconditioned or reprocessed. For example, the clinical system 510 can determine if second device data has been written to the memory 104, if a reprocessing date field of the memory 104 has been populated, etc. When the intravascular device 102 has not been reconditioned, the clinical system 510 determines that the intravascular device 102 is being reused. At step 622, the method 600 includes determining if the intravascular device 102 is within a period of time authorized for reuse (e.g., a reuse window). Step 622 can include reading the manufacture date field, the initial use date field, and/or an authorized period of reuse field from the memory 104. The clinical system 510 can determine if a current date, compared to the manufacture date and/or the initial use date, is within the authorized period of reuse. If reuse is attempted outside of the period authorized for reuse, then the intravascular device 102 is not authorized. At step 624, the method 600 includes providing an indication to a user that the intravascular device 102 is unauthorized for clinical use. The clinical system 510 can also write a diagnostic code to the memory 104 indicating that the intravascular device 102 is unauthorized because the reuse window for the intravascular device 102 has expired. For example, the clinical system 510 will modify a first unused use date field of the memory 104, write the serial number of the clinical system 510 to the memory 104, and/or write the diagnostic code. Future attempted reuse of the unauthorized intravascular device 102 can be prevented when a clinical system reads the diagnostic code. At step 608, the method 600 includes denying use of the intravascular device 102.

When the intravascular device 102 is within the reuse window, the clinical system 510 determines that the intravascular device 102 is authorized for reuse. The method 600 can include writing the current date to the reuse date field of the memory 104. Method 600 can also include writing the serial number of the clinical system 510 to the memory 104 as further information regarding reuse of the intravascular device 102. At step 618, the method 600 includes allowing use of the intravascular device 102.

If the clinical system 510 determines, at step 620, that the intravascular device 102 has been reconditioned or reprocessed, then, at step 626, the method 600 includes determining if the second security data is authentic. For example, the clinical system 510 can determine if the second MAC is authentic using the second device data. In some embodiments, the second MAC is determined to be authentic using all or some portion of the first device data and/or the second device data. If the second security data is not authentic, the intravascular device 102 is determined to be unauthorized. Similar to the first security data, the second security data can be determined to be not authentic when, for example, the data of the memory 104 is forged and/or otherwise tampered with. When the second security data is not authentic, at step 606, the method 600 includes providing an indication to a user that the intravascular device 102 is unauthorized for clinical use, as described above. At step 608, the method 600 includes denying use of the intravascular device 102.

When the second security data is authentic, at step 628, the method 600 includes determining if a reconditioned or reprocessed use date field of the memory 104 has been modified. When the reconditioned use date field has not been modified, the clinical system 510 determines that the intravascular device 102 is device that has not been used since being reconditioned. To determine if the intravascular device 102 is authorized for initial use after being reconditioned, at step 630, method 600 includes determining if the intravascular device 102 has expired. Step 630 can include reading the manufacture date field, a recondition date field, and/or an authorized period of use field from the memory 104. The clinical system 510 can determine if a current date, compared to the manufacture date and/or the recondition date, is within the authorized period of use. If the intravascular device 102 is determined to be expired, the intravascular device 102 is not authorized. At step 614, the method 600 includes providing an indication to a user that the intravascular device 102 is unauthorized for clinical use, as described above. At step 608, the method 600 includes denying use of the intravascular device 102.

When it is determined at step 630 that the intravascular device 102 has not expired, the clinical system 510 determines that the intravascular device 102 is authorized for initial use after reconditioning. At step 632, the method 600 includes writing the reconditioned use date to the memory 104. Step 632 can also include writing the serial number of the clinical system 510 to the memory 104 as further information regarding use of the intravascular device 102. At step 618, the method 600 includes allowing use of the intravascular device 102.

If, at step 628, the reconditioned use date field of the memory 104 has been modified, then the clinical system 510 determines that the reconditioned intravascular device 102 is being reused. At step 622, the method 600 includes determining if the intravascular device 102 is within a period of time authorized for reuse. Step 622 can include reading the manufacture date field, the initial use date field, the reconditioned use date field, and/or an authorized period of reuse field from the memory 104. The clinical system 510 can determine if a current date, compared to the manufacture date, the initial use date, and/or the reconditioned use date, is within the authorized period of reuse. If reuse is attempted outside of the period authorized for reuse, then the intravascular device 102 is not authorized. At step 624, the method 600 includes providing an indication to a user that the intravascular device 102 is unauthorized for clinical use, as described above. At step 608, the method 600 includes denying use of the intravascular device 102.

When, at step 622, the intravascular device 102 is within the reuse window, the clinical system 510 determines that the reconditioned intravascular device 102 is authorized for reuse. The method 600 can include writing a reuse date to the memory 104. Method 600 can also include writing the serial number of the clinical system 510 to the memory 104 as further information regarding reuse of the reconditioned intravascular device 102. At step 618, the method 600 includes allowing use of the intravascular device 102.

While the method 600 describes one instance of reuse and one instance of reconditioning, it is understood that the intravascular device 102 can be reused and/or reconditioned one, two, three, four, or more times. As such, third, fourth, and other device data and/or security data can be written to the memory 104. The intravascular device 102 can be authenticated for use in a similar manner as described with respect to the method 600.

The devices, systems, and methods described herein use MACs to prevent forgery and detect errors in the data stored on the memory 104. To determine if the intravascular device 102 is authentic, the clinical system 510 considers the contents of the memory 104 as an encrypted message sent from the manufacturer to the clinical system 510. The authentication algorithm allows the intravascular device 102 and/or computing devices (e.g., the manufacturing system 110, the reconditioning system 310, and/or the clinical system 510) to be immune from one or more forgeries. For example, the authentication algorithm can prevent a replay attack in which the same message is sent twice and accepted as authentic both times. This can occur, for example, if the MAC/memory contents from a reconditioned device are copied to a device that has yet to be reconditioned. As described above, the memory 104 can include, from manufacturing, a ROM with a unique serial number. By including the unique serial number as one of the inputs for generating the MAC, the MAC is tied to the specific memory 104 it is written on with only a negligible chance of collision.

The authentication algorithm can prevent an alteration in which some of the message is modified and accepted as authentic. When the memory 104 is written during manufacturing or during reconditioning, portions are locked to prevent any further changes. Additionally, if the values are somehow changed, an attacker would be unable to generate a new valid MAC without the secret key 208. To prevent alteration, the MAC can be configured such that a single-bit change in the input data causes roughly half the bits in the MAC to change in a manner not computationally feasible to predict (e.g., as provided for in cryptographic primitives such as block ciphers and hash functions).

The authentication algorithm can prevent a no-message attack in which a valid message/MAC pair is generated based on knowledge of other valid messages (e.g., an adaptive chosen-message attack). The secret key 208 is necessary to generate authentic MACs. The secret key 208 remains secret and is able to be changed as necessary. Such changes can be made coordination with a manufacturer's software releases for the clinical system 510. For example, the clinical system 510 can have access to an array of secret keys to authenticate the intravascular device 102, based on the serial number contained on memory 104. The manufacturer can change the secret key 208 with each new software release (e.g., for the clinical system 510) and require all newer devices (e.g., with a serial number above a cut-off value) to have a MAC based on the new key written to the memory 104 to be considered authentic. The manufacturer or authorized third party can coordinate sale of intravascular devices 102 such that devices with new serial numbers are sold to sites with clinical systems 510 that have the new software. Additionally, auto-software update can be provided for the clinical system 510, which allows for additional flexibility in changing the secret key. A brute-force attack against CMAC and AES-128 is currently held to be computationally infeasible. Thus, security against forgery can depend on the security of the secret key 208.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

While the present disclosure referred to primarily to intravascular devices, the system disclosed herein is well suited to authentication of any disposable or limited use device. One skilled in the art will recognize the application of the principles herein across other disciplines.

What is claimed is:

1. A system for managing use of intraluminal devices for placement in a patient's body, the system comprising:
   a computing device configured for communication with an intraluminal device; and
   a memory in communication with the computing device and the intraluminal device, wherein the computing device is configured to:
   determine whether first security data stored in the memory is authenticated;
   determine whether the intraluminal device has been reconditioned;
   in response to determining that the first security data is authenticated and that the intraluminal device has not been reconditioned:
   write use data to the memory, wherein the use data corresponds to a number of authenticated uses of the intraluminal device at a first time and is modified to include the first security data specific to one or more authenticated uses; and read the use data written on the memory at a second time to determine usage of the intraluminal device.

2. The system of claim 1, wherein the intraluminal device is a disposable device.

3. The system of claim 1, wherein the intraluminal device is a guidewire or a catheter.

4. The system of claim 1, wherein the memory is disposed within the intraluminal device.

5. The system of claim 1, further comprising a patient interface module in communication with and between the computing device and the memory.

6. The system of claim 3, wherein the catheter comprises at least one selected from the group consisting of: an image sensor, a pressure sensor, a flow sensor, and a combination thereof.

7. The system of claim 1, wherein the computing device is configured, in response to determining that the intraluminal device has been reconditioned, to determine whether second security data stored in the memory is authenticated, wherein the second security data is based on the first security data and reconditioning data.

8. The system of claim 7, wherein the computing device is configured:

in response to determining that the second security data is authenticated, write reconditioned use data to the memory; and in response to determining that the second security data is not authenticated, deny access to the memory.

* * * * *